United States Patent
Lagerman et al.

(10) Patent No.: US 8,666,202 B2
(45) Date of Patent: Mar. 4, 2014

(54) SYSTEM AND METHOD FOR MEASURING PROPERTIES OF A THIN FILM COATED GLASS

(75) Inventors: Jordan B. Lagerman, Spring Green, WI (US); Keith J. Burrows, Mineral Point, WI (US); Kyle R. Thering, Avoca, WI (US)

(73) Assignee: Cardinal IG Company, Eden Prairie, MN (US)

( * ) Notice: Subject to any disclaimer, the term of this patent is extended or adjusted under 35 U.S.C. 154(b) by 121 days.

(21) Appl. No.: 13/400,357

(22) Filed: Feb. 20, 2012

(65) Prior Publication Data

US 2013/0215413 A1 Aug. 22, 2013

(51) Int. Cl.
| | | |
|---|---|---|
| G02B 6/26 | (2006.01) | |
| G02B 6/42 | (2006.01) | |
| G01N 21/86 | (2006.01) | |
| G01V 8/00 | (2006.01) | |
| G01N 21/88 | (2006.01) | |

(52) U.S. Cl.
USPC .............. 385/12; 385/15; 385/16; 385/20; 385/21; 385/31; 385/39; 385/49; 356/319; 356/326; 356/445; 356/239.1; 356/239.2; 356/239.7; 250/559.01; 250/559.1; 250/559.11

(58) Field of Classification Search
USPC ............ 385/12, 20, 21, 39, 49; 356/319, 326, 356/445, 239.1, 239.2, 239.7; 250/559.01, 250/559.1, 559.11
See application file for complete search history.

(56) References Cited

U.S. PATENT DOCUMENTS

| | | |
|---|---|---|
| 3,274,882 A | 9/1966 | Krieger |
| 4,284,356 A | 8/1981 | Heilman |
| 4,727,260 A | 2/1988 | Krauth |
| 4,753,530 A * | 6/1988 | Knight et al. .................. 356/73 |
| 5,039,225 A * | 8/1991 | Uekusa ......................... 356/448 |
| 5,396,080 A | 3/1995 | Hannotiau |
| 5,754,283 A * | 5/1998 | Keane et al. ................... 356/73 |
| 6,683,695 B1 | 1/2004 | Simpson |
| 7,304,744 B1 | 12/2007 | Hatanaka |
| 7,414,738 B2 | 8/2008 | Schroder |
| 7,502,119 B2 | 3/2009 | Chalmers |

(Continued)

FOREIGN PATENT DOCUMENTS

| | | |
|---|---|---|
| DE | 4201274 | 7/1993 |
| WO | 2007103304 A2 | 9/2007 |

OTHER PUBLICATIONS

PCT International Search Report and Written Opinion dated May 14, 2013 for related Application No. PCT/US2013/026626, 14 pgs.
Solutions for the glass and solar industry from Carl Zeiss, Optoplex III P, http://www.inline-metrology.com/, taken off of web on Sep. 27, 2011, 16 pages.

(Continued)

*Primary Examiner* — Ryan Lepisto
(74) *Attorney, Agent, or Firm* — Fredrikson & Byron, P.A.

(57) ABSTRACT

A system for measuring properties of a thin film coated glass having a light source, a spectrometer, at least one pair of probes, a first optical fiber switch and a second optical fiber switch. The pair of probes includes a first probe located on one side of a glass sheet and a second probe located on the opposite side of the glass sheet, directly across from the first probe. The first and second optical fiber switches are adapted to couple either probe to the light source and/or the spectrometer. Because the design of the system is optically symmetrical, calibration may be performed without the use of a reference material such as a tile or mirror.

19 Claims, 7 Drawing Sheets

(56) References Cited

U.S. PATENT DOCUMENTS

2007/0165210 A1 7/2007 Wang et al.
2008/0180684 A1 7/2008 Chalmers et al.
2010/0220316 A1 9/2010 Finarov

OTHER PUBLICATIONS

LDLS™ Laser-Driven Light Sources EQ-99FC, Compact, Long-Life, High Brightness, Broadband Light Source with Fiber-Coupled Output brochure, http://www.energetiq.com/html/eq99FC.html, taken off of web on Jan. 31, 2012, 2 pages.

* cited by examiner

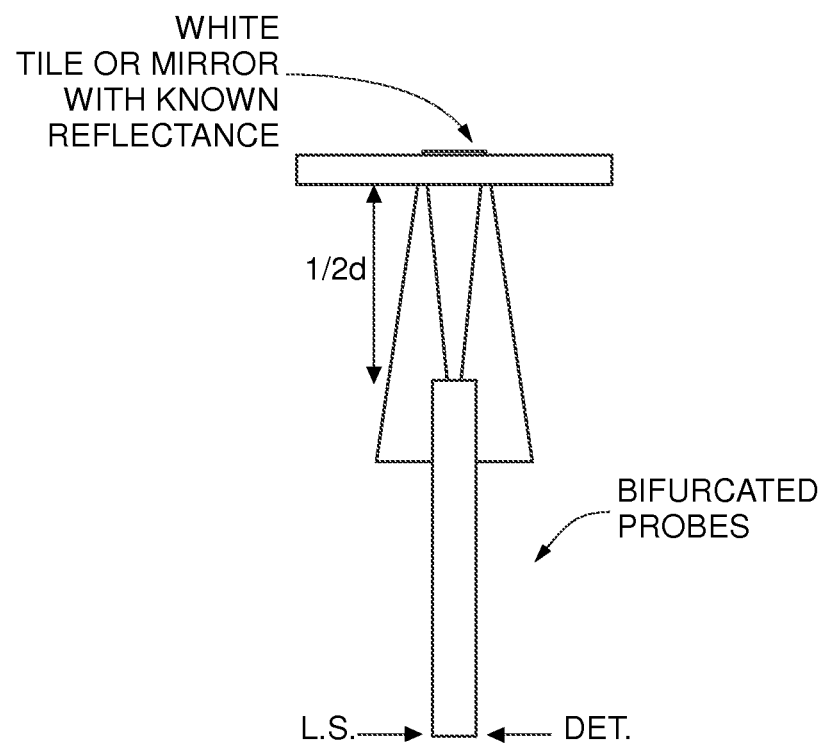

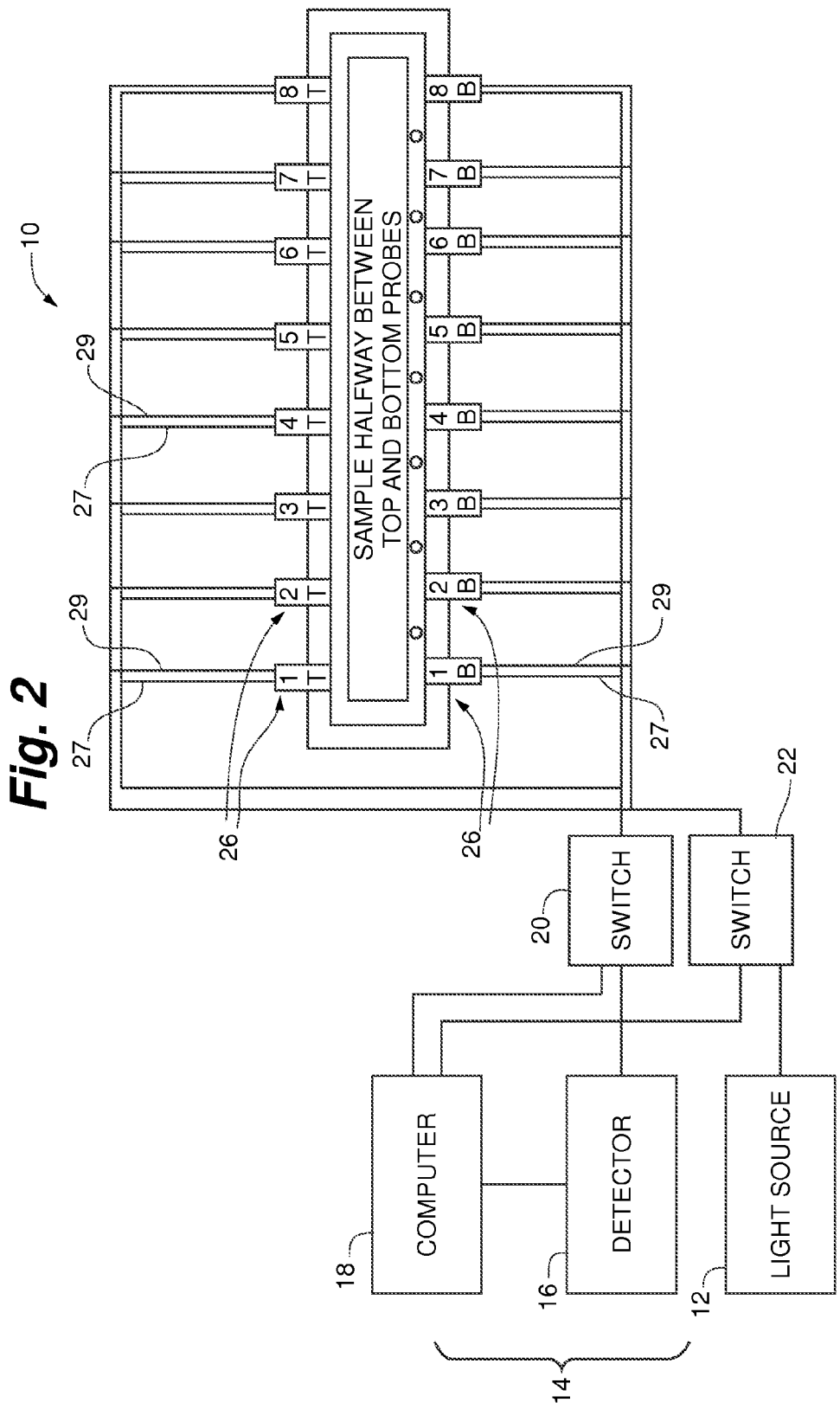

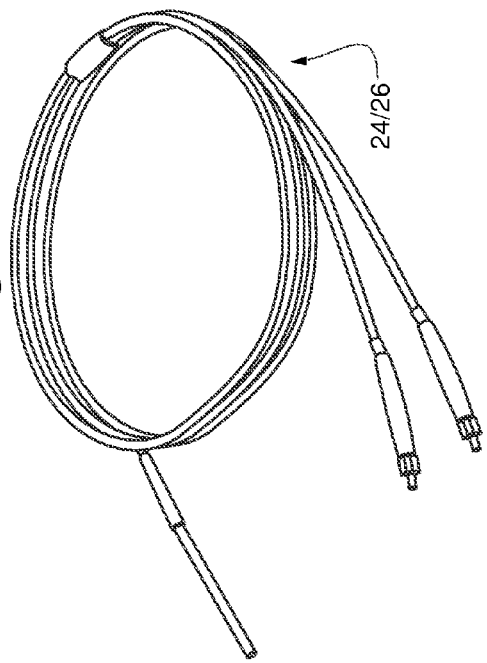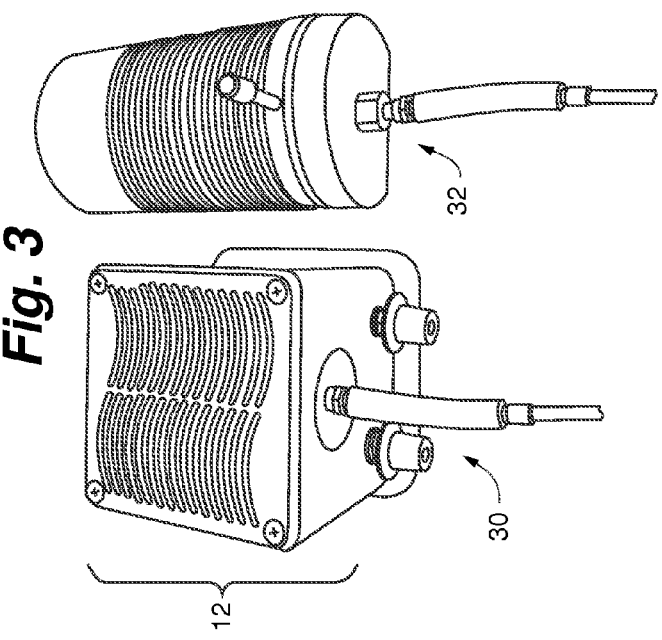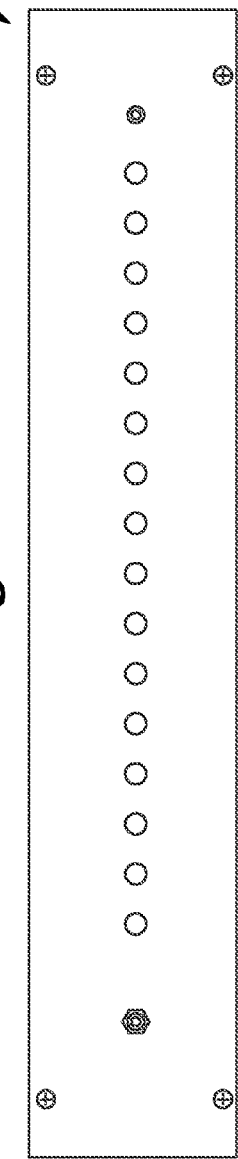

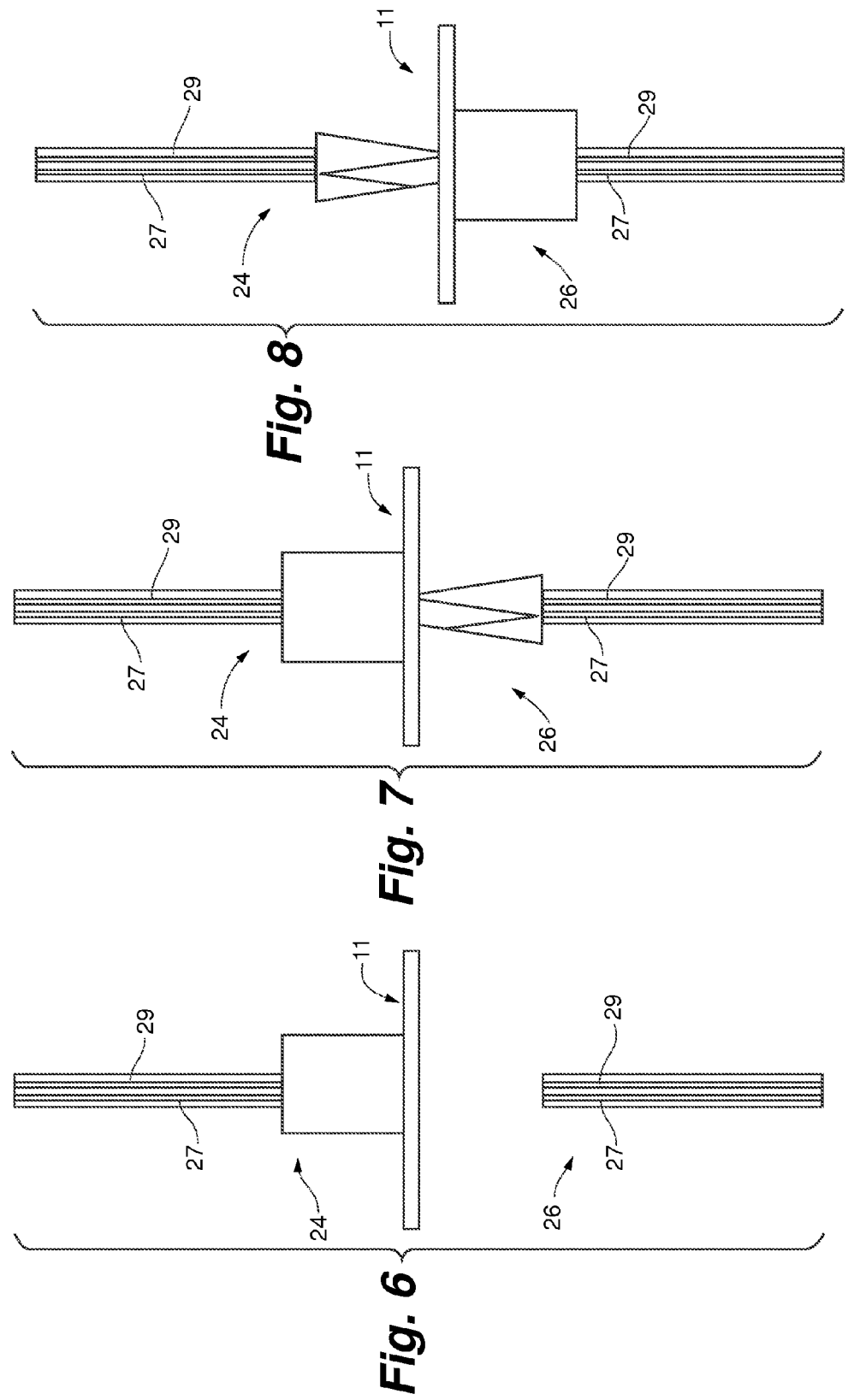

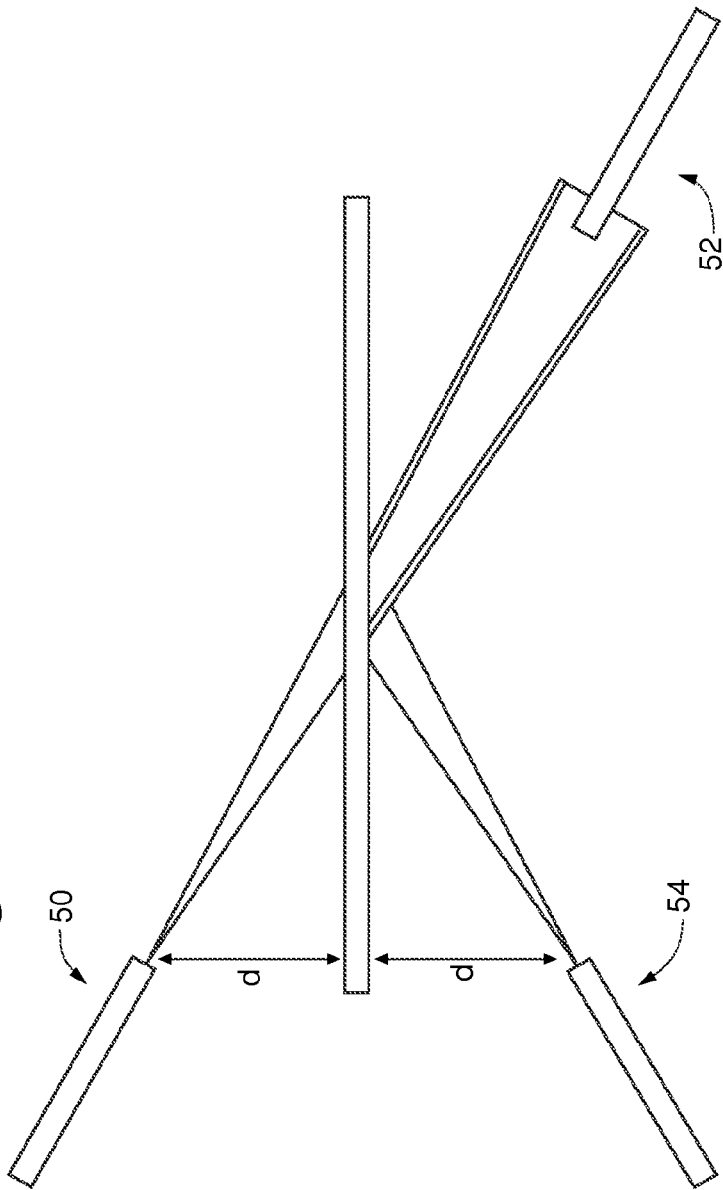

SYSTEM AND METHOD FOR MEASURING PROPERTIES OF A THIN FILM COATED GLASS

FIELD OF THE INVENTION

The embodiments of the invention are directed to a system and method for measuring properties of a thin film coated glass, and, more particularly, to a system and method that can be calibrated while in use without the need for a reference specimen such as a white tile or mirror.

BACKGROUND

Systems and methods are known for in-line measurement of optical coatings. In particular, various measurements such as spectral transmittance, spectral reflectance including color values, and sheet resistance measurements may be made on a coated glass sheet as it is being conveyed on a transport system in a coating apparatus.

An issue such systems face is that they must be calibrated to ensure the accuracies of their measurements.

In known systems using multiple probes provided along the width of the transport system, each probe has its own light source and its own spectrometer. Because a separate light source is used for each probe, to perform a reflection calibration, the industry standard is to reflect light off a reference material back to the spectrometer. The reference material can be a mirror or a white tile, for example. Because the probes are stationary, the reference material has to be brought in front of the probe as schematically shown in FIG. 1. The probe incorporates both a light source and a detector. The light is reflected off the reference material into the detector. This must be done for each probe that has its own light source. Because the reference material must either be brought in front of the probe or the probe must be moved to face the reference material, this complicates the operation of the measurement system and introduces issues with repeatability. In addition, over time, the reference material can become damaged or aged and thus not present a constant reflection standard and the calibration accuracy may therefore suffer. Also, because a separate light source and spectrometer is used for each measurement head, the reproducibility of the system decreases.

One such system is commercially offered by the Company of Carl Zeiss AG of Germany. It has an in-line system commercially referred to as the Optoplex system that can make various in-line measurements. Multiple pairs of probes are arranged both above and below the coating transport system. In particular, the OPTOPLEX III P provides in-line measurements of spectral reflectance and transmittance including color values. The data are available in real-time and displayed in several graphical modes. The OPTOPLEX III P says it has automatic self calibration. The calibration is believed to be performed in gaps between sheets of the coated glass. Because the light source always remains in the same position and it is not across from the reflection probe, it is believed that calibration is performed, like other prior art systems, using a reference material such as a tile as previously explained.

Other systems utilize one measurement head or probe that is mechanically translated across the width of the glass.

It is desirable to provide a system and method that overcomes these disadvantages.

SUMMARY

According to a first aspect of the invention, there is provided a system for measuring properties of a thin film coated glass. The system includes a light source, a spectrometer, at least one pair of probes comprising a first and a second optical probe, a first optical fiber switch and a second optical fiber switch. Each probe has a bifurcated fiber which includes a first leg and a second leg wherein each leg can either emit or collect light, the first optical probe is located above the glass and the second optical probe is located below the glass directly across from the first optical probe. The first optical fiber switch is adapted to couple the spectrometer to the first leg of each optical probe. The second optical fiber switch is adapted to couple the light source to the second leg of each optical probe. A film side reflection calibration is performed by coupling the second leg of the optical probe located below the glass to the light source and coupling the first leg of the optical probe located above the glass to the spectrometer and wherein a glass side reflection calibration is performed by coupling the light source to the second leg of the optical probe located above the glass and coupling the spectrometer to the first leg of the optical probe located below the glass thereby eliminating the need for a reference material to be located in front of the probe coupled to the light source.

According to another aspect of the invention, there is provided a method of measuring properties of a thin film coated glass. The method includes the steps of:

providing a system for measuring properties of a thin film coated glass including a light source, a spectrometer, at least one pair of probes, a first optical fiber switch, a second optical fiber switch, wherein the pair of probes include a first and a second optical probe, wherein each probe has a bifurcated fiber which includes a first leg adapted to be coupled to the first optical fiber switch and a second leg adapted to be coupled to the second fiber optical switch wherein each leg can either emit or collect light, the first optical probe is located above the glass and the second optical probe is located below the glass directly across from the first optical probe;

performing a film side reflection calibration by coupling the second leg of the second probe to the light source and coupling the first leg of the first probe to the spectrometer; and performing a glass side reflection calibration by coupling the light source to the second leg of the first probe and coupling the spectrometer to the first leg of the second probe, wherein the calibrations are performed without the need for a reference material to be located in front of the probe coupled to the light source.

The system may be used in a glass sputtering line including a transport conveyor on which the glass is transported, wherein the at least one pair of probes is located in the coater with one optical probe of the pair located above the transport conveyor and the other optical probe of the pair located below the transport conveyor directly opposite of the optical probe located above the transport conveyor, wherein the optical distance between a first side of the glass and the optical probe located above the transport conveyor and the optical distance between a second side of the glass and the optical probe located below the conveyor are optically the same.

According to another aspect of the invention, there is provided a system for measuring properties of a thin film coated glass at angles other than 90° including a light source, a spectrometer, at least three probes, a first optical fiber switch and a second optical fiber switch. The three probes include a first, a second and a third optical probe, wherein either the first or second probe can either emit light and the third probe collects light, the first optical probe is located above the glass at an angle and the second and third optical probes are located below the glass at the same angle with respect to the glass as the first optical probe with the second optical probe directly opposite to the first optical probe. The first optical fiber switch is adapted to couple the spectrometer to the third optical probe. The second optical fiber switch is adapted to couple the light source to either the first or the second optical probe. An angle measurement is performed by coupling the second optical probe to the light source and coupling the third optical probe to the spectrometer. A glass side reflection calibration is performed by coupling the first optical probe to the light source and coupling the third optical probe to the spectrometer thereby eliminating the need for a reference material to be located in front of the probe coupled to the light source.

BRIEF DESCRIPTION OF THE DRAWINGS

FIG. 1 is a schematic of a prior art calibration technique.

FIG. 2 is a schematic of an embodiment of a system for measuring properties of a thin film coated glass of the present invention.

FIG. 3 is a photograph of a light source used with the embodiments of the present invention.

FIG. 4 is a photograph of an optic probe used with the embodiments of the invention.

FIG. 5 is photograph of a switch used with the embodiments of the invention.

FIG. 6 is a schematic illustrating a transmission measurement arrangement.

FIG. 7 is a schematic illustrating a glass side reflection measurement arrangement.

FIG. 8 is a schematic illustrating a film side reflection measurement arrangement.

FIG. 12 is a schematic of an embodiment of a system for measuring optical properties of a thin film coated glass of the present invention.

DETAILED DESCRIPTION OF THE PREFERRED EMBODIMENT OF THE INVENTION

Figure 11:
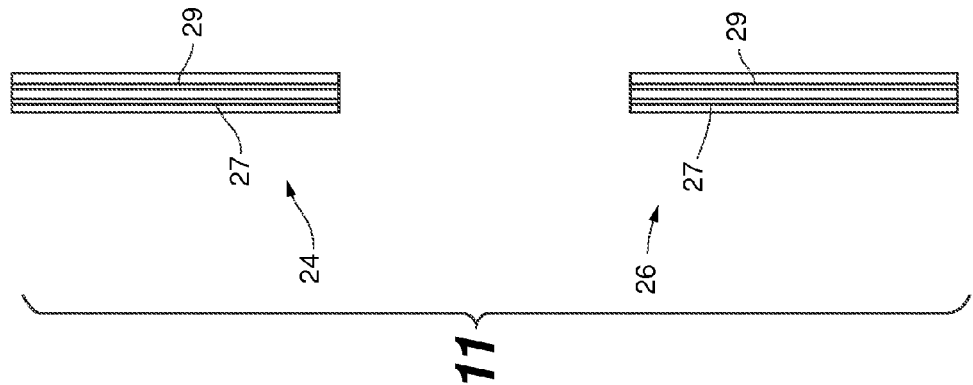
FIG. 11 is a schematic illustrating a light reference for a glass side reflection and transmission calibration arrangement.

FIG. 1 is a schematic of a prior art calibration technique. As previously mentioned, in known systems, a reference material, usually in the form of a piece of mirror or white tile, is either brought in front of the probe to perform reflectance calibration or the probe is moved to face the reference material. FIG. 1 illustrates this industry known calibration technique. A probe having a bifurcated fiber has one fiber coupled to a light source and the other fiber coupled to a spectrometer. Light from the light source is emitted by one fiber, reflected off the reference material and then collected by the other fiber. Because a separate light source is used for each probe, this calibration technique must be used for each probe which is time consuming and complicates matters. Also, because separate light sources and spectrometers are used for each measurement head, positional variations are introduced in the measurement values.

FIG. 2 is a schematic of an embodiment of a system for measuring properties of a thin film coated glass of the present invention. The system 10 may be used in-line with a glass coater or it may be used as a standalone unit. The system includes a light source 12, an analyzer 14, preferably in the form of a spectrometer 16 and a computer 18 or processor, a first fiber optical switch 20, a second fiber optical switch 22 and a plurality of pairs of probes 24 and 26. Each pair of probes 24 and 26 includes a first probe 24 and a second probe 26 located directly across from the first probe. If the system is to be used in-line, a transport means 28 such as a conveyor is located between the first and second probes of each pair of probes. The first probes 24 are located above the transport means 28 and will also be referred to throughout as the top probes and the second probes 26 are located below the transport means 28 and will be referred to throughout as the bottom probes. The first and second probes each have bifurcated fibers, meaning there is a first leg 27 and second leg 29 located in the first probe and a first leg 27 and second leg 29 located in the second probe. The first leg 27 of each of the top and bottom probes is coupled to the first fiber optical switch 20. The second leg 29 of each of the top and bottom probes is coupled to the second fiber optical switch 22. Each leg can either emit or collect light depending on how it is coupled to the remainder of the system. If the glass is coated solely on one side, preferably the coated glass 11 is located on the transport conveyor 28 so that the coated side faces away from the bottom probes 26 (i.e., towards the top probes 24). Otherwise, if the glass is coated on both sides, either side may be placed as the top side (i.e., the side facing the top heads). In addition, while a horizontal coater is illustrated, the embodiments of the present invention may be used on a vertical coating system. In addition, the embodiments of the invention need not be used necessarily solely on an in-line coater outside of a vacuum chamber but they may also be used in-situ inside a vacuum chamber of a coater, in addition, they may also be used in a standalone system.

The computer 18 or processor will run software that controls various components of the system to perform various operations. In particular, the computer 18 will control the first and second fiber optical switches 20 and 22 so that they couple a particular leg of the probe to the light source 12 and spectrometer 16 depending upon what operation is to be performed as will be described in detail hereinafter. The second fiber optical switch 22 couples second leg 29 of each probe 24 and 26 to the light source 12 and computer 18. The first fiber optical switch 22 couples the first leg 27 of each probe 24 and 26 to the spectrometer 16 and the computer 18. Thus, depending on the operation to be performed such as transmission measurement, film side reflectance measurement, film side calibration, etc., the first and second fiber optical switches 20 and 22 are activated to selectively couple the light source 12 and spectrometer 16 to particular legs of the top and/or bottom probe 24, 26 as will be described in detail hereinafter.

In a preferred embodiment, for a coater having a width of about 100 inches, the probes are about 4 to about 20 inches apart and more preferably about 12 inches apart.

FIG. 3 is a photograph of a light source 12 used with the embodiments of the present invention. In a preferred embodiment, the light source 12 includes actually two light sources 30 and 32 although that need not be the case and only one source may be used. Preferably, the light source 12 emits a light having a minimum wavelength ranging from about 380 to about 1000 nanometers, and, more preferably, having a wavelength ranging from at least about 250 to about 2,500 nanometers and, more preferably. In this particular embodiment illustrated, both a LED 30 and tungsten/halogen 32 light source are used. The outputs of each of the light sources are joined together through a common fiber (not shown). The LED 30 is used to boost the light source in the blue green region of about 400 to about 525 nanometers. Any optic fiber may be coupled to the light source. Alternatively, a laser driven light source, such as a xenon lamp, may be used. Otherwise, either a tungsten/halogen light source may be used as previously described or, alternatively, a tungsten light source alone or a halogen light source alone, with or without an LED may be used.

FIG. 4 is a photograph of an optic probe 24 or 26 that may be used as either the top or bottom probe in the system according to the embodiments of the invention. As previously mentioned, each probe 24, 26 has bifurcated fibers 27 and 29 so that it can both emit and collect light depending on how they are coupled to the remainder of the system. A second leg 29 of the bifurcated fiber is coupled to the second fiber optical switch 22 and the first leg 27 of the bifurcated fiber is coupled to the first fiber optical switch 20. While the probes are described as having bifurcated fibers, each of the bifurcated fibers may, in fact, be made up of multiple fibers itself.

FIG. 5 is photograph of a fiber optical switch that may be used as the first or second fiber optical switch 20 and 22 in the embodiments of the invention. If, for example, the illustrated switch is used the first fiber optical switch 20, then only the first leg 27 of the bifurcated fiber of each probe 24 and 26 is coupled to a connection on the switch and the second leg 29 of the bifurcated fiber is coupled to the second fiber optical switch 22.

Light sources, optical probes, spectrometers and switches that may be used in the embodiments of the system are commercially available from many sources such as Avantes, Leoni, Gulf Fiberoptics, Ocean Optics and BWTEK, Jenoptik, CVI Melles Groit, StellarNet, Thor Labs, MightEx and Energetiq, for example.

FIG. 6 is a schematic illustrating a transmission measurement arrangement. With the glass located between the pairs of probes, second leg 29 of the bottom probes are coupled to the light source 12 and first leg 27 of the top probes are coupled to the spectrometer 16. To perform this measurement operation, the computer 18 directs the second fiber optical switch 22 to couple the light source 12 to the second leg 29 of the bottom probes and directs the first fiber optical switch 20 to couple the first leg 27 of the top probes to the spectrometer 16. Of course the direction could be reversed with the second leg 29 of the top probes coupled to the light source 12 and the first leg 27 of the bottom probes coupled to the spectrometer 16.

FIG. 7 is a schematic illustrating a glass side reflection measurement arrangement. With the glass located between the pairs of probes, the second and first legs 29 and 27 of the bottom probes are coupled to both the light source 12 and the spectrometer 16, respectively, while the first and second legs of the top probes are not coupled to anything. To perform this measurement operation, the computer 18 directs the second fiber optical switch 22 to couple the light source 12 to the second leg 29 of the bottom probes and directs the first fiber optical switch 20 to couple the first leg 27 of the bottom probes to the spectrometer 16.

FIG. 8 is a schematic illustrating a film side reflection measurement arrangement. With the glass located between the pairs of probes, the top probes are coupled to both the light source 12 and the spectrometer 16 while the bottom probes are not coupled to anything. To perform this measurement operation, the computer 18 directs the second fiber optical switch 22 to couple the light source 12 to the second leg 29 of the top probes and directs the first fiber optical switch 20 to couple the first leg 27 of the top probes to the spectrometer 16.

Using the system depicted in FIG. 2, it only takes about 0.1 to about 0.2 seconds to measure transmission and glass and film side reflectance.

In order for measurements to remain accurate, the system 10 must be calibrated. Reflectance calibrations in known systems, as previously mentioned, were made using a reference material such as a mirror or a white tile that was either placed in front of the probe or the probe was moved to face the reference material. Light was emitted from the probe and reflected off the reference material, collected by the probe and sent to the spectrometer. When the reflection off glass is measured, it is corrected back to this reference material. The reference material provided the light reference and has been an industry standard for years.

In the embodiments of the invention, because the entire measurement system of the probes and fibers is optically symmetrical, the optical path lengths are virtually identical, and thus the need for a reference material in performing calibration is eliminated. As already described, the light source and the spectrometer may be coupled to the first and second legs of each bifurcated fiber of the top or the bottom probes and the gap between the glass and the top probe and the gap between the glass and the bottom probe is kept substantially the same distance.

For every probe position, a dark reference and a light reference must be collected in order to have proper transmission and reflection readings. For the dark reference, the light source is not used so the probes are exposed only to ambient light. The spectrometer would be coupled to a probe of each pair of probes and the ambient light collected by the probe is measured by the spectrometer. This measurement is referred to as the dark reference. Next, a light reference needs to be measured. The light reference indicates the total possible light that may be received for a measurement. For this measurement, the light source is coupled to a second leg 29 of either the top or bottom probe and the spectrometer 16 is coupled to the first leg 27 of the probe opposite to that coupled to the light source. As previously mentioned, a reference material was used to provide the light reference reflection. In the embodiments of the present invention, the need for such a reference material is eliminated as will be described hereinafter.

Figure 9:
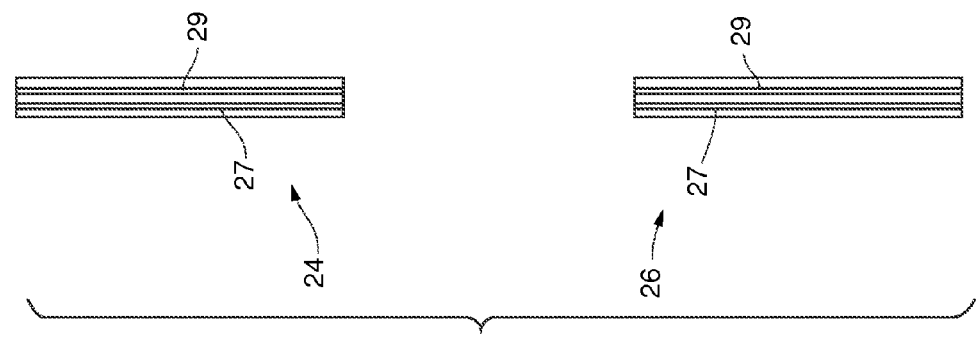
FIG. 9 is a schematic illustrating a dark reference calibration arrangement.

FIG. 9 is a schematic illustrating a dark reference calibration arrangement. With no glass located between the pairs of probes, the first leg 27 of the top probe is coupled to the spectrometer 16 and a measurement of ambient light conditions is made. Then the first leg 27 of each bottom probe is coupled to the spectrometer 16 and another measurement of ambient conditions is made.

The value obtained in this dark calibration is set as 0%. To perform this calibration operation, the computer 18 directs the first fiber optical switch 20 to couple the first leg 27 of the top probes to the spectrometer 16 and then directs the first fiber optical switch 20 to couple the first leg 27 of the bottom probes to the spectrometer 16.

Figure 10:
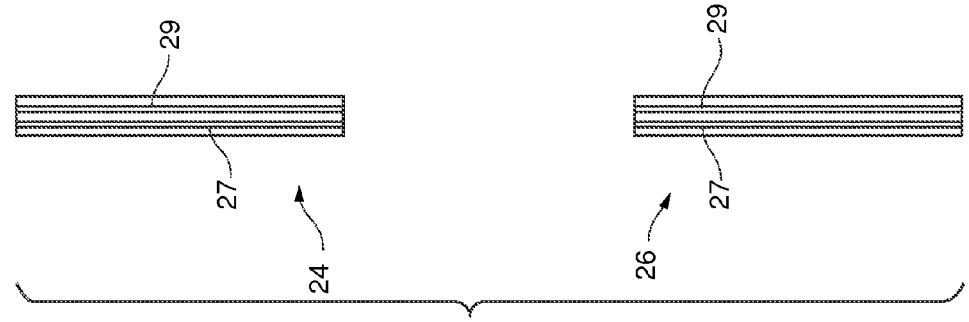
FIG. 10 is a schematic illustrating a light reference for a film side reflection and transmission calibration arrangement.

FIG. 10 is a schematic illustrating a light reference for a film side reflection and transmission calibration arrangement. With no glass located between the pairs of probes, the second leg 29 of the bottom probes are coupled to the light source 12 and the first leg 27 of the top probes are coupled to the spectrometer 16. To perform this calibration operation, the computer 18 directs the second fiber optical switch 22 to couple the light source 12 to the second leg 29 of the bottom probes and directs the first fiber optical switch 20 to couple the first leg 27 of the top probes to the spectrometer 16. With regard to the film side reflection calibration, imagine a prior art system using a reference material such as a mirror. If a mirror was placed halfway between the top and bottom probe, light directed from the top probe would be reflected by the mirror and collected by the top probe. Using the arrangement shown in FIG. 10, light is directed from the bottom probe to the top probe and has the same optical path length with the same divergence as light reflected off the mirror, thus eliminating the need for a reference material.

FIG. 11 is a schematic illustrating a light reference for a glass side reflection and transmission calibration arrangement. With no glass located between the pairs of probes, the bottom probes are coupled to the spectrometer 16 and the top probes are coupled to the light source 12. To perform this calibration operation, the computer 18 directs the second fiber optical switch 22 to couple the light source 12 to the second leg 29 of the bottom probes and directs the first fiber optical switch 20 to couple the first leg 27 of the top probes to the spectrometer 16. Of course the direction could be reversed and the top probes are coupled to the light source 12 and the bottom probes are coupled to the spectrometer 16. This calibration is the opposite of the film side calibration previously described.

Another advantage of the embodiments of the present invention is that because no moving parts are used in the measuring positions, unlike systems that use a reference material for calibration, the system may be more suitable in environments with a vacuum.

FIG. 12 is a schematic of an embodiment of a system for measuring glass side refection at a given angle of the present invention. Preferably various angle optical measurements may be made using similar principles as previously discussed with head-on measurements. The angles may vary from 45°, 60° and 75°, for example. In this embodiment, three probes are utilized as illustrated. One top probe 50 and two bottom probes 52 and 54 are used for each measurement position. The top probe 50 and the bottom probe 54 are coupled to a first fiber optical switch which is coupled to a light source so that either the top probe 50 or the bottom probe 54 may emit a beam of light depending upon the instructions provided to the first fiber optical switch and the other bottom probe 52 is coupled to a second fiber optical switch that is coupled to the spectrometer. One of the bottom probes 52 is coupled to the spectrometer and the other bottom probe 54 is coupled to the light source for measurement operations, otherwise, the light source would be coupled to the top probe 50 for calibration operations. Again, the system is optically symmetrical so there is no need for reference materials to perform a calibration operation. Thus, when a measurement operation is performed, the light source is coupled to the bottom probe 54 and it is redirected to the other bottom probe 52 which is coupled to the spectrometer. When a calibration operation is performed, the top probe 50 is coupled to the light source and it is directed to the bottom probe 52 which is coupled to the spectrometer to simulate a reflecting mirror or constant reflection standard.

Figure 13:
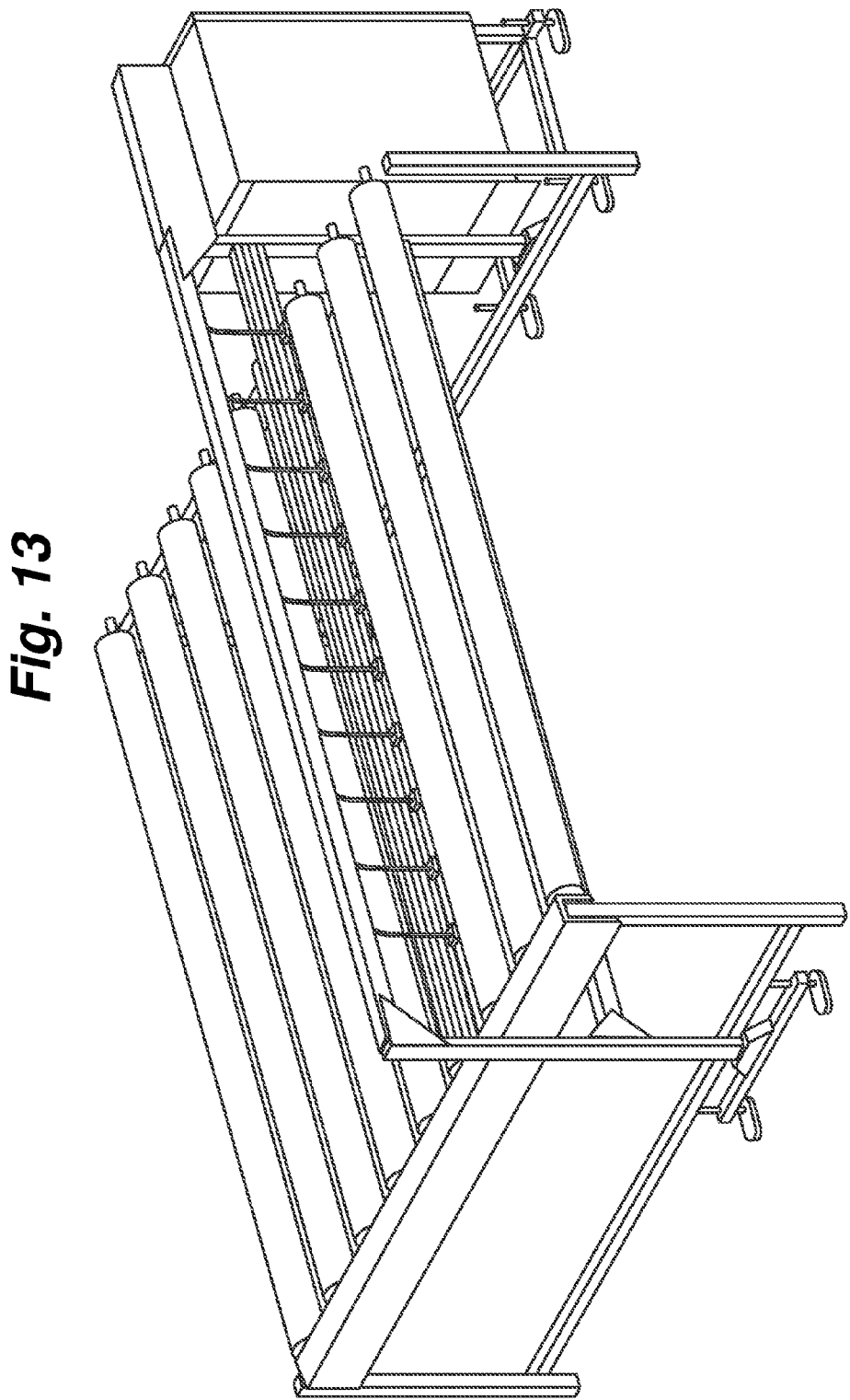
FIG. 13 is a perspective illustration of a portion of an embodiment of the measurement system according to the present invention.

FIG. 13 is a perspective illustration of a portion of an embodiment of the measurement system according to the present invention. The glass itself is not illustrated. It can be seen that there is a top rack that holds the top probes and a bottom rack that holds the bottom probes directly opposite of the top probes. The distance between the top rack an the bottom rack may be adjusted by adjusting their position on the side frames of the system. The measurement system may be incorporated into a coating line or other environment such as a vacuum chamber by any well known technique.

What is claimed is:

1. A system for measuring properties of a thin film coated glass, comprising:
   a light source;
   a spectrometer;
   at least one pair of probes comprising a first and a second optical probe, wherein each probe has a bifurcated fiber which includes a first leg and a second leg wherein each leg can either emit or collect light, the first optical probe is located above the glass and the second optical probe is located below the glass directly across from the first optical probe;
   a first optical fiber switch adapted to couple the spectrometer to the first leg of each optical probe;
   a second optical fiber switch adapted to couple the light source to the second leg of each optical probe, wherein a film side reflection calibration is performed by coupling the second leg of the optical probe located below the glass to the light source and coupling the first leg of the optical probe located above the glass to the spectrometer and wherein a glass side reflection calibration is performed by coupling the light source to the second leg of the optical probe located above the glass and coupling the spectrometer to the first leg of the optical probe located below the glass thereby eliminating the need for a reference material to be located in front of the probe coupled to the light source.

2. The system of claim 1 wherein the light source comprises a tungsten/halogen light source.

3. The system of claim 1 wherein the light source emits a light having a wavelength ranging from at least about 250 to about 2500 nanometers.

4. The system of claim 1 wherein the light source emits a light having a wavelength ranging from about 300 to about 1000 nanometers.

5. The system of claim 2 further comprising a light emitting diode added to the light source to increase the light source's wavelength in the region of about 400 to about 525 nanometers.

6. The system of claim 1 wherein a measurement of glass side reflectance may be made by coupling the light source to the second leg of the first probes and coupling the first leg of the second probes to the spectrometer.

7. The system of claim 1 wherein a measurement of film side reflectance may be made by coupling the light source to the second leg of the first probes and coupling the first leg of the first probes to the spectrometer.

8. The system of claim 1 wherein a measurement of glass side transmission may be made by coupling the light source to the second leg of the second probes and coupling the first leg of the first probes to the spectrometer.

9. The system of claim 1 further comprising a processor coupled to the switch wherein the processor performs a glass side reflection calibration routine by coupling the light source to the second leg of the first optical probe and coupling the spectrometer to the first leg of the second optical probe and the processor performs a film side reflection calibration routine by coupling the light source to the second leg of the second optical probe and coupling the spectrometer to the first leg of the first optical probe.

10. The system of claim 9 wherein the processor performs a transmission measurement routine by coupling the light source to the second leg of either the first or second optical probe and coupling the spectrometer to the optical probe opposite that of the optical probe coupled to the light source.

11. The system of claim 9 wherein the processor performs a film side reflection measurement routine by coupling the light source to the first leg of the first optical probe and coupling the spectrometer to the second leg of the first optical probe.

12. The system of claim 11 wherein the processor performs a glass side reflection measurement routine by coupling the light source to the second leg of the second optical probe and coupling the spectrometer to the first leg of the second optical probe.

13. The system of claim 1 further comprising a plurality of pairs of additional probes spanning a width of the glass, wherein each of the additional probes has a bifurcated fiber with a first leg coupled to the first switch and a second leg coupled to the second switch.

14. A method of measuring properties of a thin film coated glass comprising:
   providing a system for measuring properties of a thin film coated glass including a light source, a spectrometer, at least one pair of probes, a first optical fiber switch, a second optical fiber switch, wherein the pair of probes include a first and a second optical probe, wherein each probe has a bifurcated fiber which includes a first leg adapted to be coupled to the first optical fiber switch and a second leg adapted to be coupled to the second fiber optical switch wherein each leg can either emit or collect light, the first optical probe is located above the glass and the second optical probe is located below the glass directly across from the first optical probe;
   performing a film side reflection calibration by coupling the second leg of the second probe to the light source and coupling the first leg of the first probe to the spectrometer; and
   performing a glass side reflection calibration by coupling the light source to the second leg of the first probe and coupling the spectrometer to the first leg of the second probe, wherein the calibration are performed without the need for a reference material to be located in front of the probe coupled to the light source.

15. The system of claim 1 further comprising a glass sputtering line including a transport conveyor on which the glass is transported, wherein the at least one pair of probes is located in-line with the coater with one optical probe of the pair located above the transport conveyor and the other optical probe of the pair located below the transport conveyor directly opposite of the optical probe located above the transport conveyor, wherein the optical distance between a first side of the glass and the optical probe located above the transport conveyor and the optical distance between a second side of the glass and the optical probe located below the conveyor are optically the same.

16. The system of claim 1 wherein the light source is a laser driven light source.

17. The system of claim 16 wherein the laser driven light source is a xenon light source.

18. The system of claim 1 further comprising a glass sputtering line including a transport conveyor on which the glass is transported, wherein the at least one pair of probes is located in-situ with the coater with one optical probe of the pair located above the transport conveyor and the other optical probe of the pair located below the transport conveyor directly opposite of the optical probe located above the transport conveyor, wherein the optical distance between a first side of the glass and the optical probe located above the transport conveyor and the optical distance between a second side of the glass and the optical probe located below the conveyor are optically the same.

19. A system for measuring properties of a thin film coated glass, comprising:
   a light source;
   a spectrometer;
   at least three probes comprising a first, a second and a third optical probe, wherein either the first or second probe can either emit or collect light and the third probe collects light, the first optical probe is located above the glass at an angle and the second and third optical probes are located below the glass at the same angle with respect to the glass as the first optical probe with the second optical probe directly opposite to the first optical probe;
   a first optical fiber switch adapted to couple the spectrometer to the third optical probe;
   a second optical fiber switch adapted to couple the light source to either the first or the second optical probe, wherein an angle measurement is performed by coupling the second optical probe to the light source and coupling the third optical probe to the spectrometer and wherein a glass side reflection calibration is performed by coupling the first optical probe to the light source and coupling the third optical probe to the spectrometer thereby eliminating the need for a reference material to be located in front of the probe coupled to the light source.

* * * * *